(12) United States Patent
Franken et al.

(10) Patent No.: US 10,123,972 B2
(45) Date of Patent: Nov. 13, 2018

(54) FIBER COMPRISING A BIODEGRADABLE POLYMER

(71) Applicant: DSM IP Assets B.V., TE Heerlen (NL)

(72) Inventors: Astrid Franken, Echt (NL); George Mihov, Echt (NL); Jens Christoph Thies, Echt (NL)

(73) Assignee: DSM IP ASSETS, B.V., Heerlen (NL)

( * ) Notice: Subject to any disclaimer, the term of this patent is extended or adjusted under 35 U.S.C. 154(b) by 0 days.

(21) Appl. No.: 15/484,488

(22) Filed: Apr. 11, 2017

(65) Prior Publication Data

US 2017/0216201 A1  Aug. 3, 2017

Related U.S. Application Data

(60) Division of application No. 14/975,156, filed on Dec. 18, 2015, which is a continuation of application No. 14/115,146, filed as application No. PCT/EP2012/058036 on May 2, 2012, now abandoned.

(30) Foreign Application Priority Data

May 2, 2011 (EP) ..................................... 11164501

(51) Int. Cl.
| | | |
|---|---|---|
| *A61K 47/34* | (2017.01) | |
| *A61K 9/00* | (2006.01) | |
| *A61K 9/70* | (2006.01) | |
| *D01F 1/10* | (2006.01) | |
| *D01F 6/82* | (2006.01) | |
| *D01F 6/62* | (2006.01) | |
| *C08G 69/44* | (2006.01) | |

(52) U.S. Cl.
CPC .......... *A61K 9/0051* (2013.01); *A61K 9/0019* (2013.01); *A61K 9/70* (2013.01); *A61K 47/34* (2013.01); *C08G 69/44* (2013.01); *D01F 1/10* (2013.01); *D01F 6/625* (2013.01); *D01F 6/82* (2013.01); *D10B 2331/02* (2013.01); *D10B 2331/041* (2013.01); *D10B 2401/12* (2013.01)

(58) Field of Classification Search
CPC .... A61K 47/34; A61K 9/0019; A61K 9/0051; A61K 9/70; C08G 69/44
See application file for complete search history.

(56) References Cited

FOREIGN PATENT DOCUMENTS

WO    2007/035938 A2 *    3/2007

OTHER PUBLICATIONS

Li et al. (Nano Letters, vol. 5, No. 5, Published 2005, pp. 913-916) (Year: 2005).*

* cited by examiner

*Primary Examiner* — Alma Pipic
(74) *Attorney, Agent, or Firm* — Kevin M. Bull

(57) ABSTRACT

The present disclosure relates to fibers implantable in the body of a human or animal and processes for manufacturing such a fiber. The fiber undergoes a reduction in surface area to volume ratio of a factor of 1.05-10 upon injection in the human or animal body. In an embodiment, a process for manufacturing a fiber comprises extruding a biodegradable polymer into a fiber capable of fitting in a syringe needle of at least 25 Gauge, and cooling the fiber below its dry glass transition temperature while the fiber is under tension.

8 Claims, 3 Drawing Sheets

Influence of the fiber remodeling

FIBER COMPRISING A BIODEGRADABLE POLYMER

Figure 1:
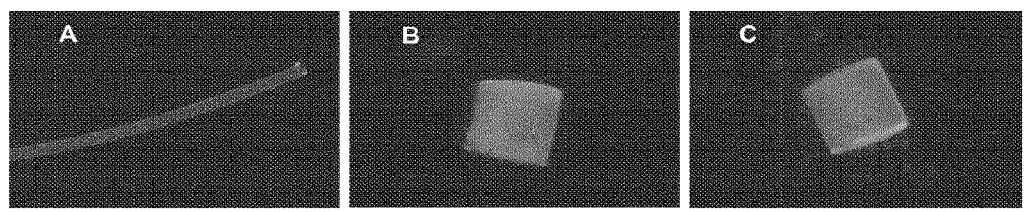

This application is a divisional of U.S. application Ser. No. 14/975,156 filed on Dec. 18, 2015, which is a continuation of U.S. application Ser. No. 14/115,146 filed Feb. 18, 2014, which is the US National Phase application of International Application No. PCT/EP2012/058036 filed May 2, 2012, which designated the US and claims priority to European application number 11164501.6, filed May 2, 2011, the entire contents of each of which are hereby incorporated by reference.

The present invention relates to a fiber comprising a biodegradable polymer which undergoes dimensional change. The present invention further relates to the use of the fiber as a drug delivery vehicle for the treatment of ophthalmic diseases.

The present invention also relates to a process for the manufacturing of a fiber via melt extrusion.

The present invention is based on the premise that the fibers can be formulated as drug delivery vehicles that may incorporate a bioactive agent for delivery to the anterior and/or posterior segment of the eye in a consistent and reliable manner. Release will depend on diffusion of bioactive agent through the polymer matrix and biodegradation of the polymer.

Intraocular delivery of drugs is a particular problem. The eye is divided into two chambers; the anterior segment which is the front of the eye, and the posterior segment which is the back of the eye. Diseases of the anterior segment are easier to treat with formulations such as eye drops because they can be applied topically. For example, glaucoma can be treated from the front of the eye. Diseases of the retina, such as diabetic retinopathy and macular degeneration, are located in the posterior segment and are difficult to treat because drugs applied topically, such as eye drops, typically do not penetrate to the back of the eye. Drugs for these diseases have customarily been delivered by injection directly into the back of the eye. These injections often have to be repeated to provide therapeutic doses of said drugs for the required duration of the therapy, but this is very uncomfortable for the patient. There is thus a need for drug delivery vehicles which allow an easy, safe and more comfortable injection, while providing an increase duration of sustained drug delivery.

Moreover there is a need in the art for new and better controlled delivery of a variety of different types of bioactive agents to target specific body sites, such as the exterior and interior tissues of the eye. In particular, there is a need in the art for more efficacious delivery vehicles for continuous delivery of ophthalmologic agents to the anterior or posterior segment of the eye over a sustained period of time, for example in treatment of chronic diseases of the front and back of the eye.

Surprisingly it has been found that the above disadvantages can be overcome providing a fiber comprising a biodegradable polymer which undergoes dimensional change upon injection in the human or animal body wherein the dimensional change is a reduction of the surface area to volume ratio of a factor ranging from 1.05-10, preferably ranging from 1.25-5, more preferably ranging from 1.5-4, most preferably ranging from 2 to 10.

The fiber of the present invention thus has the ability to physically reshape or remodel after being injected into the human or animal body. The dimensional change leads to an improved sustained release of bioactive agents due to the change of the surface to volume ratio, as diffusion of the bioactive agent from the bulk through the surface will be slowed by a relative reduction of the surface area. It moreover will decrease the number of injections needed to release the required amount of bioactive agents. A further advantage is that a fibers can be injected that may even remodel into a drug delivery depot, which drug delivery depot as such would never be injectable.

The fiber according to the present invention is sized for injection via a pharmaceutical syringe needle having a bore of at least 25 Gauge. In general the fibers may have a size ranging from 100-250 μm.

The fiber according to the present invention comprises a biodegradable polymer, preferably a biodegradable polymer which is an amorphous biodegradable polymer. By amorphous is meant that the molecules are oriented randomly and are intertwined, much like cooked spaghetti in which the polymer has a glasslike, transparent appearance. Whether or not polymers are amorphous can easily be determined by a man skilled in the art and may be measured using DSC or X-ray diffraction as is known in the art.

The biodegradable polymer preferably has a dry Tg ranging from 45 to 60 C. Further the biodegradable polymer preferably has a wet Tg below 37 C. Dry and wet Tg can be measured according to ASTM test method NO. D3418.

Examples of biodegradable polymers are polyesteramides or polyhydroxyacids (for example PLGA or poly L,D-lactic acid).

An example of an amorphous biodegradable polymer is a polyesteramide comprising alpha-amino acids, dials and dicarboxylic acids building blocks.

Preferably the fiber comprises a polyesteramide comprising alpha-amino acids, dials and dicarboxylic acids building blocks.

More preferred the fibers comprise a polyesteramide according to formula I

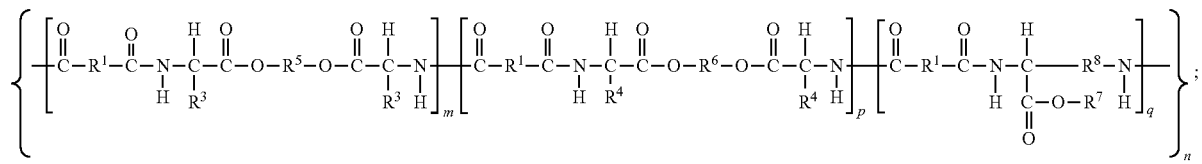

Formula I wherein m is about 0.01 to about 0.99; p is about 0.99 to about 0.01; and q is about 0.99 to about 0.01; and wherein n is about 5 to about 350; and wherein $R_1$ is independently selected from the group consisting of $(C_2\text{-}C_{20})$alkylene, $(C_2\text{-}C_{20})$alkenylene, —$(R_9$—CO—O—$R_{10}$—O—CO—$R_9)$—, —$CHR_{11}$—O—CO—$R_{12}$—$COOCR_{11}$— and combinations thereof;

$R_3$ and $R_4$ in a single co-monomer m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —$(CH_2)SH$, —$(CH_2)_2S(CH_3)$, —$CH_2OH$, —$CH(OH)CH_3$, —$(CH_2)_4NH_3+$, —$(CH_2)_3NHC(=NH_2+)NH_2$, —$CH_2COOH$, —$(CH_2)COOH$, —$CH_2$—$CO$—$NH_2$, —$CH_2CH_2$—$CO$—$NH_2$, —$CH_2CH_2COOH$, $CH_3$—$CH_2$—$CH(CH_3)$—, $(CH_3)_2$—$CH$—$CH_2$—, $H_2N$—$(CH_2)_4$—, Ph-$CH_2$—, $CH=C$—$CH_2$—, $HO$-p-Ph-$CH_2$—, $(CH_3)_2$—$CH$—, Ph-$NH$—, $NH$—$(CH_2)_3$—$C$—, $NH$—$CH=N$—$CH=C$—$CH_2$—.

$R_5$ is selected from the group consisting of $(C_2-C_{20})$alkylene, $(C_2-C_{20})$alkenylene, alkyloxy or oligoethyleneglycol;

$R_6$ is a bicyclic-fragments of 1,4:3,6-dianhydrohexitols $R_7$ is hydrogen, $(C_6-C_{10})$ aryl, $(C_1-C_6)$ alkyl or a protecting group;

$R_8$ is independently $(C_1-C_{20})$ alkyl or $(C_2-C_{20})$alkenyl;

$R_9$ or $R_{10}$ are independently selected from $C_2-C_{12}$ alkylene or $C_2-C_{12}$ alkenylene.

$R_{11}$ or $R_{12}$ are independently selected from H, methyl, $C_2-C_{12}$ alkylene or $C_2-C_{12}$ alkenylene.

Even more preferred the fiber comprises a polyesteramide of Formula III, further disclosed as PEA-III-Ac Bz wherein m is about 0.3, p is about 0.45, q is about 0.25, n is about 5-100 and wherein $R_1$ is $(CH_2)_8$;
$R_3$ and $R_4$ are selected from $(CH_3)_2$—$CH$—$CH_2$—;
$R_5$ is selected from $(CH_2)_6$;
$R_6$ is 1,4:3,6-dianhydrosorbitol (DAS);
$R_7$ is a benzyl protecting group;
$R_8$ is $(CH_2)_4$.

A more extended description of PEA-III-Ac Bz is poly-8-[(L-Leu-DAS)$_{0.45}$(L-Leu-6)$_{0.3}$-L-Lys(Bz)]$_{25}$. The fractions indicate overall fractions of the monomers in the synthesis.

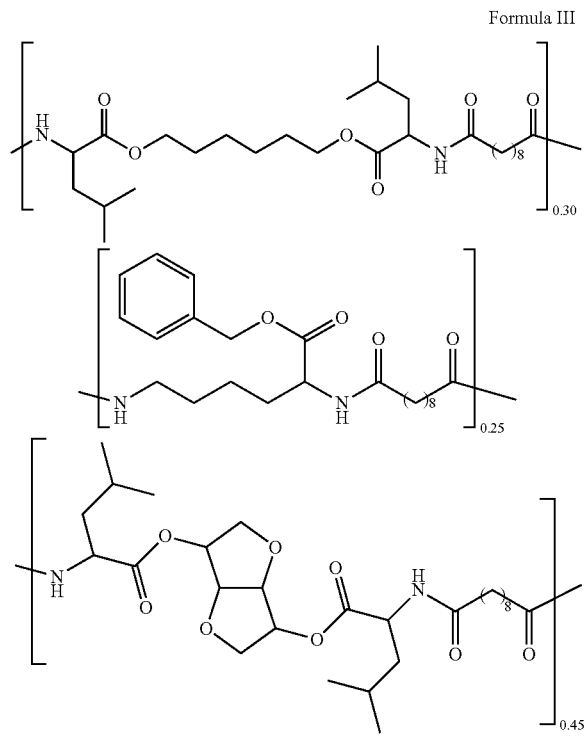

Formula III

PEA III Ac Bz

As used herein, the term "alkyl", refers to a straight or branched chain hydrocarbon group including methyl, ethyl, n-propyl, isopropyl, n-butyl, isobutyl, tert-butyl, n-hexyl, and the like.

As used herein, "alkenyl" or "alkenylene", refers to structural formulas herein to mean a divalent branched or unbranched hydrocarbon chain containing at least one unsaturated bond in the main chain or in a side chain.

As used herein. "alkynyl", refers to straight or branched chain hydrocarbon groups having at least one carbon-carbon triple bond.

The term "aryl" is used with reference to structural formulas herein to denote a phenyl radical or an ortho-fused bicyclic carbocyclic radical having about nine to ten ring atoms in which at least one ring is aromatic. Examples of aryl include, but are not limited to, phenyl, naphthyl, and nitrophenyl.

At least one of the alpha-amino acids used in the co-polymers is a natural alpha-amino acid. For example, when the $R_3$s or $R_4$s are $CH_2Ph$, the natural alpha-amino acid used in synthesis is L-phenylalanine. In alternatives wherein the $R_3$s or $R_4$s are $CH_2$—$CH(CH_3)_2$, the co-polymer contains the natural amino acid, leucine. By independently varying the $R_3$s and $R_4$s within variations of the two co-monomers as described herein, other natural alpha-amino acids can also be used, e.g., glycine (when the $R_3$s or $R_4$s are H), alanine (when the $R_3$s or $R_4$s are $CH_3$), valine (when the $R_3$s or $R_4$s are $CH(CH_3)_2$), isoleucine (when the $R_3$s or $R_4$s are $CH(CH_3)$—$CH_2$—$CH_3$), phenylalanine (when the $R_3$s or $R_4$s are $CH_2$—$C_6H_5$), lysine (when the $R_3$s or $R_4$s $(CH_2)_4$—$NH_2$); or methionine (when the $R_3$s or $R_4$s are —$(CH_2)_2S(CH_3)$, and mixtures thereof.

The PEA co-polymers preferably have an average number molecular weight (Mn) ranging from 15,000 to 200,000 Daltons. The PEA co-polymers described herein can be fabricated in a variety of molecular weights and a variety of relative proportions of the two bis-(alpha amino acid)-containing units and optional Lysine-based monomer of the co-polymer. The appropriate molecular weight for a particular use is readily determined by one of skill in the art. A suitable Mn will be in the order of about 15,000 to about 150,000 Daltons, for example from about 30,000 to about 80,000 or from about 35,000 to about 75,000. Mn is measured via GPC in THF with polystyrene as standard.

Other examples of a biodegradable polymers include, but are not limited to, polyester amides, polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(trimethylene carbonate), polyphosphazenes, poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), poly(ethylene glycol) (PEG), copoly(ether-esters) (e.g. PEO/PLA), polyalkylene oxides such as poly(ethylene oxide), poly(propylene oxide), poly (ether ester), polyalkylene oxalates, poly(aspirin), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof.

The fiber according to the present invention may further comprise at least a bioactive agent. The bioactive agent can be any agent which is a therapeutic, prophylactic, or diagnostic agent. Such bioactive agent may include without any limitation small molecule drugs, peptides, proteins, DNA, cDNA, RNA, sugars, lipids and whole cells. The bioactive agents can have antiproliferative or anti-inflammatory properties or can have other properties such as antineoplastic, antiplatelet, anti-coagulant, anti-fibrin, antithrombotic, antimitotic, antibiotic, antiallergic, or antioxidant properties. Examples of antiproliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include ABT-578, 40-0-(3-hydroxy)propyl-rapamycin, 40-O-[2-(2-hydroxy)ethoxy]ethyl-rapamycin, and 40-0-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and nonsteroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck AND Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting.

The fiber according to the present invention can be used as a drug eluting vehicle especially for the treatment of disease in ophthalmology.

The invention further relates to the process for the manufacturing of the fiber according to the present invention comprising the following process steps;
 a. extruding the biodegradable polymer into a fiber fitting in a syringe needle of at least 25 Gauge
 b. which fiber while under tension is cooled below its dry glass transition temperature The fiber is preferably manufactured via an extrusion process for example melt extrusion in which the biodegradable polymer and eventual additional compounds are homogenised using a Retsch cryomill. The resulting powder is then filled into a pre-heated DSM Xplore micro-extruder with 5 cc barrel size and twin-screws which is connected to a micro fiber spin device. The biodegradable polymer preferably has a residence time of 5-10 min at 120 C-140° C. before it is to be stretched into a fiber with diameter in the range of 100-250 µm. The extrusion is normally performed under inert atmosphere in order to minimize the oxidative degradation of the polymer during the process. Under tension it is subsequently cooled at room temperature. The obtained fiber is then preferably cut into pieces from for example 4 mm and may be sterilized via gamma radiation under cooling conditions.

In FIG. 1 the dimensional change of the injected fiber according to the present invention is shown.

FIG. 1 relates to a PEA III fiber dry (A, 25× magn.), in rabbit vitreous after 1 day (B, 50× magn.) and after 14 days (C, 50× magn.)

It showed a decrease of the surface area to volume ratio of the fiber i.e., increase in fiber diameter from 150 µm to about 300 µm, with associated decrease in fiber length while maintaining a relatively constant volume.

Figure 2:
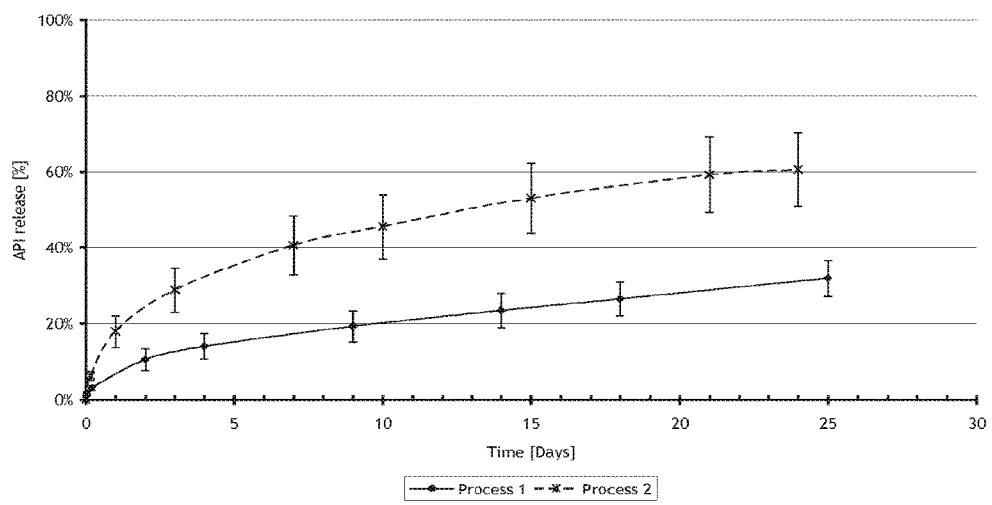

FIG. 2 relates to the release of active pharmaceutical ingredients (API) from PEA-III Ac Bz fibers.

Figure 3:
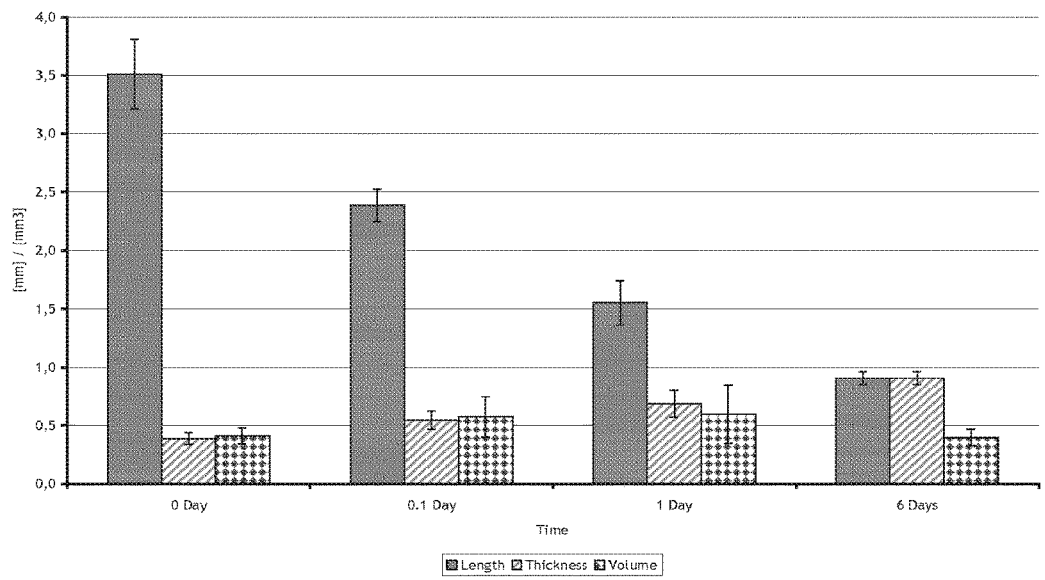

FIG. 3 shows the evolution of the length, thickness and volume of a PEA-III Ac Bz fiber containing 30 wt % API.

Figure 4:
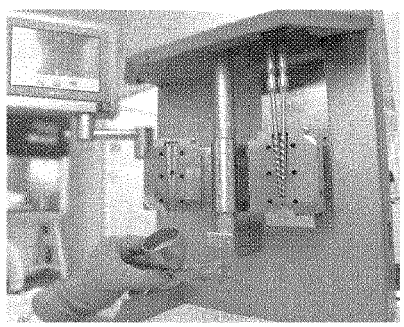

FIG. 4, relates to a DSM Pharma extruder Xcelera for twin-screw micro extrusion with a speed of 1-250 rpm, a temperature range of 20-400° C., a marximal torque of 9000N and a barrel capacity of 2 or 5 cm$^3$ equipped with DSM micro fiber spin device for thin fiber spinning.

Figure 5:
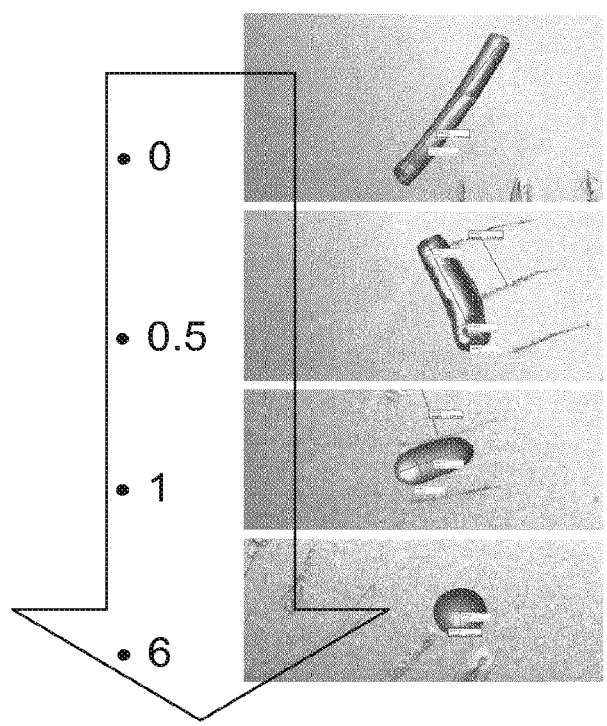

FIG. 5 shows pictures of the fibers at 0, 0.5, 1 and 6 days taken using optic microscopy. On the optical light microscopy pictures is represented the size evolution of a PEA fiber containing 30 wt % of API, after immersion in PBS.

The invention will now be further and specifically described by the following examples.

Materials

PEA-III-Ac Bz polymers are used in the following examples. A more extended description of PEA-III-Ac Bz is poly-8-[(L-Leu-DAS)$_{0.45}$(L-Leu-6)$_{0.3}$-L-Lys(Bz)]$_{0.25}$. Structure is given in Formula III. The fractions indicate overall fractions of the monomers in the synthesis.

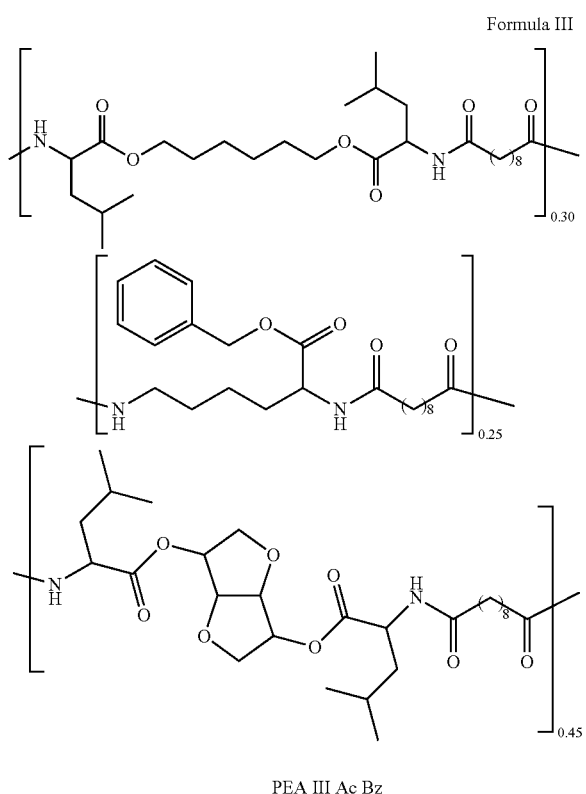

Formula III

PEA III Ac Bz

Synthesis of PEA III Ac Bz

Trietylamine (30.9 mL, 0.222 mole, 2.2 eq) and N,N-dimethylformamide (53.07 mL, 0.689 mole) were added to a mixture of Di-OSu-sebacinate (39.940 g, 0.1008 mole, 1.0 eq), L-leucine(6)-2TosOH (20.823 g, 0.0302 mole, 0.30 eq), L-leucine-(DAS)-2TosOH (32.503 g, 0.0453 mole, 0.45 eq) and L-lysine(Bz)-2TosOH (14.628 g, 0.0252 mole, 0.25 eq) in a nitrogen flushed 500 mL round bottomed flask equipped with a overhead stirrer at room temperature. The subsequent mixture was heated to 60° C. to allow the reaction to proceed and monitored by GPC analysis in THF. After 36 hours a stable molecular weight was obtained, subsequently a portion of L-leucine(6)-2TosOH (4.338 g, 0.0063 mole) along with triethylamine (1.76 mL, 0.0126 mole) and N,N-dimethylformamide (4.54 mL, 0.0590 mole) was added to terminate the polymerization reaction. The mixture was heated additionally for 24 hours after which the viscous solution was further diluted with N,N-dimethylformamide (407.85 g, 5.301 mole) and allowed to cool to room temperature. At room temperature acetic anhydride (1.89 mL, 0.0199 mole) was added to acylate the amino functional end groups of the polymer. The mixture was stirred at room temperature for 24 hours. In scheme 1 the general reaction is shown.

Scheme 1: Reaction scheme for the synthesis of PEA III Ac Bz.

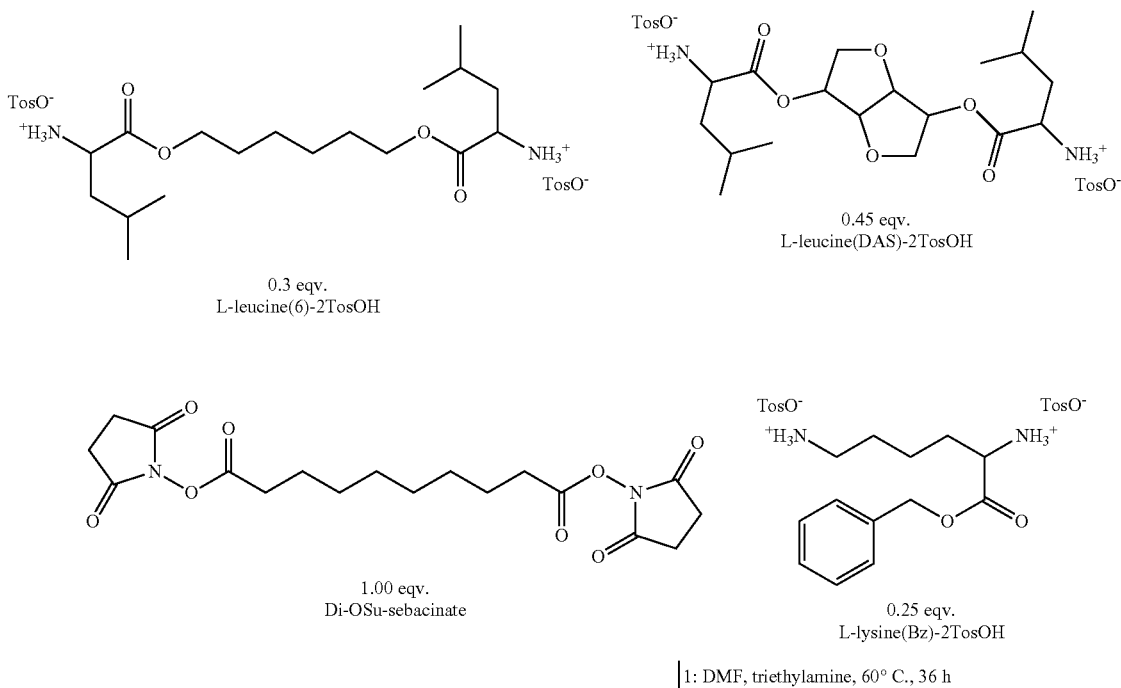

-continued

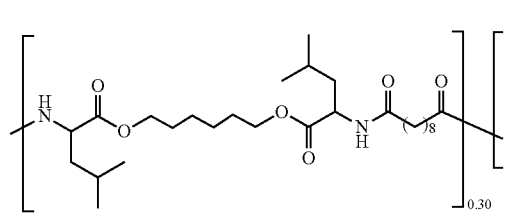 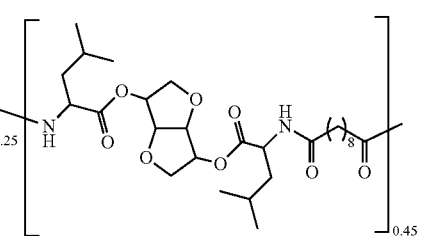

The obtained crude polymer mixture was precipitated in water in a 10:1 ratio (water:reaction mixture). The polymer was collected and dissolved in ethanol (500 mL, 8.57 mole) and the procedure was repeated a second time. The polymer was again dissolved in ethanol (500 mL, 8.57 mole) and precipitated in ethylacetate (5000 mL, 50.91 mole) by drop wise addition to a stirring solution. The precipitated polymer was washed with two portions ethylacetate (100 mL, 1.00 mole), dried and dissolved in ethanol (500 mL, 8.57 mole) and filtered over a 0.2 μm PTFE membrane filter. The filtered polymer solution was dried under reduced pressure at 65° C.

Yield 75%, Mn=50 kDa (Gel Permeation Chromatography (GPC) in THF relative to polystyrene standards. Glass transition temperatures were determined by Differential Scanning calorimetry (DSC). Measurements were taken from second heating, with a heating rate of 10° C./min., Tg=48° C.

EXAMPLE 1

0.52 g of API (Active Pharmaceutical Ingredient) and 4.31 g of PEA III Ac Bz were co-dissolved in ethanol, film-casted and allowed to dry. Films were subsequently cryo-milled. The uniformed cryomilled formulation was processed into a fiber at a Pharma mini-extruder shown on FIG. 3. The cryo-milled powder was melt-extruded at a temperature of 125° C., using a twin-screw extruder. The extruder dye was of 0.75 mm. Extruded polymer was spin at a speed of 5 m/min to 5 m/min and thereafter cooled at room temperature, under nitrogen.

The resulting fibers of a diameter of ~300 μm were cut with a length of 10 mm and individually weight. The release was performed at 37° C. in PBS. PBS was refreshed at each time point and quantity of API was measured in triplicate, by HPLC. Upon immersion in PBS at 37° C., these fibers undergo remodeling (Process 1) Resulting release is presented in the FIG. 2

COMPARATIVE EXAMPLE A 0.03 g of API and 0.25 g of polymer were co-dissolved in 2.5 ml of methanol, film-casted and allowed to dry. Resulting films were cut into fibers of a length of 5-6 mm and a thickness of 250 μm. Release of API was performed on individually weighted fibers, releasing in PBS at 37° C. PBS was refreshed at each time point and quantity of API was measured in triplicate by HPLC.

Upon immersion in PBS at 37° C., these fibers do not remodel (Process 2)

Resulting release is presented in the FIG. 2.
Results

Approximately 50% of API is released in 15 days from fibers without remodeling while only 20% of API is released, at the same time point, from fibers with remodeling.

This example shows that a fiber remodeling inducing a decrease of the surface to volume ratio will influence and slow down the release of API from the fiber.

EXAMPLE 2

2.13 g of API and 5.00 g of PEA III Ac Bz were co-dissolved in ethanol, film-casted and allowed to dry. Films were subsequently cryo-milled. The cryo-milled powder was melt-extruded at a temperature of 115° C., using a twin-screws extruder. The extruder dye was of 0.75 mm. Extruded polymer was spin at a speed of 5 m/min to 15 m/min and thereafter cooled at room temperature, under nitrogen.

The resulting fibers were cut and placed into PBS at 37° C. Length and thickness were monitored by optical light microscopy.

FIG. 3 represents the evolution of length, thickness, and volume of a PEA III Ac Bz fiber, containing 30 wt % API processed as described in example 1.

This figure shows that fibers' length decrease, thickness increase but the volume stays constant. There is not any swelling of the fiber but a remodeling that result on a different surface to volume ratio than initially.

The invention claimed is:

1. A process for the manufacturing of a fiber comprising a biodegradable polymer comprising the following steps:
   a. extruding a biodegradable polymer into a fiber capable of fitting in a syringe needle of at least 25 Gauge, and
   b. cooling the fiber below its dry glass transition temperature while the fiber is under tension,
   wherein the biodegradable polymer is a polyesteramide of formula I

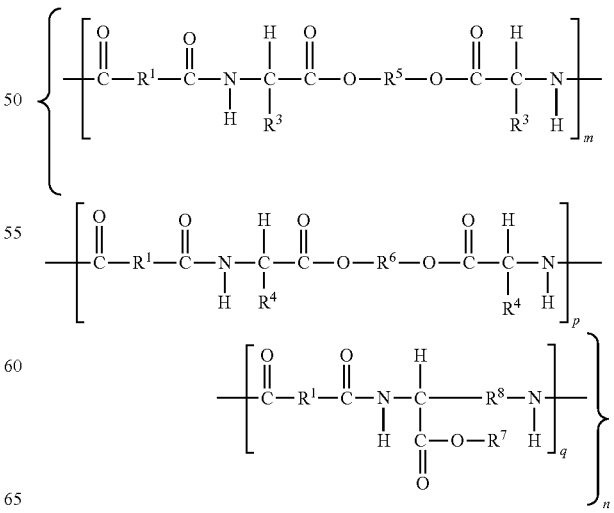

wherein m is 0.01 to 0.99; p is 0.99 to 0.01; and q is 0.99 to 0.01; n is 5 to 350;

$R^1$ is independently selected from the group consisting of $(C_2-C_{20})$alkylene, $(C_2-C_{20})$alkenylene and combinations thereof;

$R^3$ and $R^4$ in a single co-monomer m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl-$(CH_2)SH_2$, —$(CH_2)_2S(CH_3)$, —$CH_2OH$, —$CH(OH)CH_3$, —$(CH_2)_4NH_3+$, —$(CH_2)_3NHC(NH_2+)NH_2$, —$CH_2COOH$, —$CH_2$—CO—$NH_2$, —$CH_2CH_2$—CO—$NH_2$, —$CH_2CH_2COOH$, $CH_3$—$CH_2$—$CH(CH_3)$—, $(CH_3)_2$—CH—$CH_2$—, $H_2N$—$(CH_2)_4$—, Ph-$CH_2$—, $CH_2$=C—$CH_2$—, HO-p-Ph-$CH_2$—, and Ph-NH—;

$R^5$ is of $(C_2-C_{20})$alkylene, $(C_2-C_{20})$alkenylene, alkyloxy, or oligoethyleneglycol;

$R^6$ is a bicyclic-fragment of 1,4:3,6-dianhydrohexitol;

$R^7$ is hydrogen, $(C_6-C_{10})$ aryl, $(C_1-C_6)$ alkyl, or a protecting group; and $R^8$ is independently $(C_1-C_{20})$ alkyl or $(C_2-C_{20})$alkenyl;

wherein the fiber undergoes a reduction in surface area to volume ratio of a factor of 1.05-10 upon injection in the human or animal body.

2. The process according to claim 1, wherein m is about 0.3, p is about 0.45, and q is about 0.25;

n is about 5-100;

$R^1$ is $(CH_2)_8$ or $(CH_2)_4$;

$R^3$ and $R_4$ are $(CH_3)_2$—CH—$CH_2$—;

$R^5$ is $(CH_2)_6$;

$R^6$ is 1,4:3,6-dianhydrosorbitol (DAS);

$R^7$ is a benzyl protecting group; and $R^8$ is $(CH_2)_4$.

3. The process according to claim 1, wherein the biodegradable polymer has a wet Tg below 37° C.

4. The process according to claim 1, wherein the biodegradable polymer is an amorphous biodegradable polymer.

5. The process according to claim 1, wherein the fiber further comprises a bioactive agent.

6. The process according to claim 5, wherein the fiber further comprises a prodrug.

7. The process according to claim 1, further comprising the step of stretching the fiber to a diameter of from 100 to 250 μm prior to cooling the fiber below its dry glass transition temperature.

8. The process according to claim 7, wherein the biodegradable polymer has a residence time of 5 to 10 minutes at 120 to 140° C. prior to stretching the fiber.

* * * * *